(12) United States Patent
Santanach-Delisau et al.

(10) Patent No.: US 8,685,448 B2
(45) Date of Patent: Apr. 1, 2014

(54) PHARMACEUTICAL SOLID DOSAGE FORM

(75) Inventors: Angel Santanach-Delisau, Barcelona (ES); Luis Soler Ranzani, Barcelona (ES); Pierandrea Esposito, Barcelona (ES)

(73) Assignee: Laboratorios Del Dr. Esteve, S.A., Barcelona (ES)

( * ) Notice: Subject to any disclaimer, the term of this patent is extended or adjusted under 35 U.S.C. 154(b) by 0 days.

(21) Appl. No.: 13/508,460

(22) PCT Filed: Nov. 5, 2010

(86) PCT No.: PCT/EP2010/066925
§ 371 (c)(1),
(2), (4) Date: May 10, 2012

(87) PCT Pub. No.: WO2011/054930
PCT Pub. Date: May 12, 2011

(65) Prior Publication Data
US 2012/0231074 A1    Sep. 13, 2012

(30) Foreign Application Priority Data
Nov. 7, 2009   (EP) ..................... 09175339

(51) Int. Cl.
*A61K 9/20* (2006.01)
(52) U.S. Cl.
CPC .................... *A61K 9/2054* (2013.01)
USPC ........................................................ 424/465
(58) Field of Classification Search
None
See application file for complete search history.

(56) References Cited

U.S. PATENT DOCUMENTS

| 2005/0042277 A1* | 2/2005 | Srinivas et al. ............... 424/452 |
| 2006/0051421 A1 | 3/2006 | Shterman et al. |
| 2009/0004281 A1* | 1/2009 | Nghiem et al. ............... 424/490 |
| 2010/0183710 A1* | 7/2010 | Bolugoddu et al. .......... 424/456 |

FOREIGN PATENT DOCUMENTS

| EP | 0 244 380 B1 | 1/1993 |
| EP | 733 025 A1 | 6/1995 |
| EP | 0 652 872 B1 | 11/2000 |
| EP | 1 185 254 B1 | 4/2003 |
| EP | 1 086 694 B1 | 8/2006 |
| EP | 1 020 460 B1 | 7/2009 |
| WO | WO 99/48498 A1 | 9/1999 |
| WO | WO 2004/016242 A2 | 2/2004 |
| WO | WO 2009/043926 A2 | 4/2009 |

OTHER PUBLICATIONS

Famotidine tablet (Daily Med) p. 1 (2007) (http://dailymed.nlm.nih.gov/dailymed/lookup.cfm?setid=991d2b13-f491-4a25-8ea7-5136d0585874).*
International Search Report issued by the International Searching Authority (ISA/O.E.P.M.) on Nov. 29, 2011 in connection with International Application No. PCT/EP2010/066925.

* cited by examiner

*Primary Examiner* — Bethany Barham
(74) *Attorney, Agent, or Firm* — Gary J. Gershik; Cooper & Dunham LLP

(57) ABSTRACT

The present invention is directed to a solid dosage form comprising (i) a core comprising a benzimidazole; (ii) a separating layer comprising a water soluble polymer and glyceryl monostearate; and (iii) an enteric coating.

12 Claims, 2 Drawing Sheets

TAPAT       SENSE TAP

40°C / 75% HR

PHARMACEUTICAL SOLID DOSAGE FORM

This application is a §371 national stage application of PCT International Application No. PCT/EP2010/066925, filed Nov. 5, 2010, claiming priority of European Patent Application No. EP 09 175 339.2, filed Nov. 7, 2009, the contents of all of which are hereby incorporated by reference into this application.

FIELD OF THE INVENTION

The present invention relates to a pharmaceutical oral solid dosage form comprising a physiologically active compound, a separating layer and an enteric coating, to a method for preparing the same and uses thereof.

BACKGROUND OF THE INVENTION

A number of compounds used in the pharmaceutical industry, including active pharmaceutical ingredients (APIs), are labile in acid media. This causes numerous problems when it comes to developing a pharmaceutical formulation for oral administration due to the fact that when said acid labile compounds come into contact with the stomach content, which is a strongly acidic environment, degradation occurs. To avoid contact between acid labile compounds and gastric juice after oral administration of said compounds, solid pharmaceutical dosage forms have been developed that comprise a bead that contains the acid labile compound and an external layer that constitutes a gastro-resistant coating, also known as enteric coating. See, for example, chapters 45, 46, 47 of "Remington, the science and practice of pharmacy", 21$^{st}$ Edition, 2005, Ed. Lippincott Williams & Wilkins, for a discussion on coatings, concretely, pages 932-933 regarding enteric coatings. However, said gastro-resistant coatings are frequently acid and therefore the acid labile compounds need to be protected. Examples of this situation are benzimidazole compounds, of which omeprazol [(±)-5-methoxy-2-[(4-methoxy-3,5-dimethylpyridin-2-yl)methylsulfinyl]-3H-benzoimidazole] is its most representative example, and which are APIs widely known as effective gastric acid secretion inhibitors. Benzimidazol compounds of biological interest also include pantoprazole, rabeprazole, lansoprazole or (−)-(S)-5-methoxy-2-[(4-methoxy-3,5-dimethylpyridin-2-yl)methylsulfinyl]-3H-benzoimidazole, also known as esomeprazol (EP 652872), which is the levorotatory enantiomer of omeprazol.

A solution to the acid lability problem has been to introduce a separating layer between the acid labile compounds and the gastro-resistant coating. For example, EP 1020460 B1 discloses a pellet of esomeprazole sodium having a separating layer with hydroxypropyl methylcellulose as unique ingredient and an enteric coating comprising hydroxypropyl methylcellulose phtalate.

EP 244380, EP 733025, EP 1086694 and EP1185254 disclose omeprazole formulations having a separating layer comprising hydroxypropyl methylcellulose.

A different solution is to create an alkaline environment around the acid labile compound by, for example, using alkaline salts of the compound and/or incorporating a compound of alkaline reaction in the pharmaceutical solid dosage form (see, for example, EP 0 244 380 and U.S. Pat. No. 4,786,505).

Other documents also describe separating layers when formulating acid labile APIs.

However, in addition to the stability problem in acid media, some compounds, e.g. esomeprazol sodium salt, are extremely soluble in water, which makes their formulation very difficult, especially when using the aqueous layering process. This process comprises dispersing/dissolving the API and the rest of the pharmaceutical ingredients in water and making a spray-dry process or a fluid bed pulverization process at 40° approximately. When preparing the dosage form, said compounds migrate to the separating layer, or even to the enteric coating, due to their solubility in the water used in the process. This is detrimental to the stability of the compounds as it places them in contact with the acidic environment of the enteric coating.

As a consequence, the problems of avoiding the protonic transfer from the enteric coat to the core that contains the acid labile compound, or of avoiding the migration of the acid labile compound from an internal layer to an external one turn to be an important concern.

Thus, in order to provide a suitable formulation of acid labile compounds, there is an existing need to avoid both, the migration of the acid labile compounds to outer coating layers, but also the proton transfer from said outer layers to the internal layer containing the acid labile active ingredient. In order to achieve this the separating layer should be readily soluble in water, as it has to be dissolved in the human body (once the enteric coat is dissolved, in the neutral or nearly neutral pH conditions of the intestine, the API has to be released fast), but at the same time it should effectively act as a barrier in order to stop proton transfer to the core and avoid API migration to the enteric coat. Either of these unwanted migrations will affect negatively to the API's stability.

The aqueous layering process frequently used to apply the separating layer, exposes it to water and relative high temperatures (usually up to 50° C.) and, thus, makes it vulnerable to migration of water, dissolution or dispersion of the layer during the process. Also care should be taken when the enteric coat is applied over the separating layer, in order to avoid water migration through the same or into de core. Many separating layers have been tested (hydroxypropyl methylcellulose alone (HPMC), Polyvinyl Alcohol, etc. ... ) in order to avoid the above mentioned problems. However, no completely satisfactory configuration has been proposed.

BRIEF DESCRIPTION OF THE INVENTION

The inventors have now found that the provision of a separating layer comprising a water soluble polymer and glyceryl monostearate is surprisingly effective in stabilizing physiologically active compounds. It has been found that the provision of such separating layers improves their stability during formation of the dosage form and its overall stability once formed. The inventors have found that the dosage forms of the invention described below are especially useful for stabilizing acid labile and/or water soluble physiologically active compounds.

In particular the dosage forms of the invention prove to be efficient in avoiding the above mentioned problem of migration, either of the protons from outer layers to internal layers, or of the acid labile active ingredient from the inner layer to the external layer.

According to one aspect, the present invention is directed to a pharmaceutical oral solid dosage form (dosage form of the invention), preferably in the form of pellets or granules, comprising (i) a core comprising a physiologically active compound; (ii) a separating layer comprising a water soluble polymer and glyceryl monostearate; and (iii) an enteric coating.

The glyceryl monostearate present in the separating layer prevents the degradation of the acid labile active ingredient present in the core following the above mentioned mechanisms. In particular glyecryl monostearate proves to be efficient to solve the problem underlying the present invention, whereas other polymers known to exhibit the same function proved to be inefficient. This is the case for example of polyvinyl alcohol polymer. In the same manner talc used in the separating layer, as disclosed in the examples of WO-2004/016242 also failed to avoid degradation of the acid labile active ingredient in the same conditions.

According to a second aspect, the invention is directed to a process for the preparation of the dosage form of the invention comprising an aqueous layering process.

A third aspect is the dosage form of the invention for use as a medicament.

A fourth aspect is a dosage form of the invention for use in the treatment and/or prevention of a disease or condition selected from the group consisting of digestive ulcer, gastritis, reflux esophagitis, eradication of *H. pylori*, suppression of gastrointestinal bleeding caused by digestive ulcer, acute stress ulcer and hemorrhagic gastritis, suppression of gastrointestinal bleeding caused by invasive stress, ulcer caused by non-steroidal anti-inflammatory agent, gastric hyperacidity and ulcer caused by postoperative stress.

A fifth aspect is a tablet comprising one or more pharmaceutically acceptable excipients and one or more dosage forms of the invention.

A sixth aspect is a capsule or sachet comprising one or more dosage forms of the invention.

DETAILED DESCRIPTION OF THE INVENTION

Core

The core of the dosage forms of the invention contain a physiologically active compound, which is selected from active pharmaceutical ingredients (APIs). In an embodiment of the invention said physiologically active compound is an acid labile compound. In a further embodiment said physiologically active compound is a water soluble compound. In order to determine the solubility of physiologically active compounds, standard solubility tests are performed, which include the steps of:
1.—weighting 10.0 mg of the compound and adding 1 ml of the solvent (water). Stirring for up to 10 minutes. If dissolution is not complete, applying ultrasounds for up to 10 minutes.
2.—If the compound does not dissolve after step 1.—, add 1 ml portions of solvent (water), until 10 ml have been added. If dissolution is not complete, add 10 ml portions until a volume of 101 ml has been reached. If dissolution is not complete, stop the experiment and consider the compound "almost insoluble".
3.—If the compound has dissolved at some stage in step 2.—, start the experiment with 100.0 mg instead of 10.0 mg, and follow the same procedure of step 2.—.
4.—If the 100.0 mg of compound of step 3.—, dissolve in 1 ml start the experiment with 1.0 g, instead of 100.0 mg, and follow the same procedure of step 2.—. If 1.0 g of the compound is dissolved in 1 ml, stop the experiment and consider the compound "very soluble" (solubility below 1 ml/g).

Every time solvent is added, stir for up to 10 minutes, further apply ultrasounds for up to 10 minutes, if necessary. The temperature is maintained at 20° C. The experiment is finished once total dissolution is observed. At such point the amount of compound is compared with the amount of solvent (water) which has been necessary for dissolution. In an embodiment of the invention the physiologically active compound has a water solubility below 1000 ml/g, more particularly below 100 ml/g, and more particularly below 50 ml/g.

In a particular embodiment, the dosage form of the invention comprises an API.

As understood in the present invention, "acid labile compound" refers to a compound having a half-life under 10 minutes in an aqueous solution of pH less than 4, and/or a half-life between 10 minutes and 65 hours in an aqueous solution with a pH of 7. Half life is measured following standard methods which include dissolving the compound in water at a given pH to a concentration of 0.4 mg/ml (initial concentration of the sample), while maintaining a temperature of 20° C. Every 13 minutes the concentration of the sample is measured by UPLC analysis, determining the "concentration versus time" curve. Then the half-life for the compound is calculated for each pH by extrapolating from the curve the time at which concentration of the sample is 50% with respect of the initial concentration of the sample. UPLC analysis are performed using Acquity™ UPLC (Waters) equipped with a 5.0 cm×0.21 cm 1.7 µm Acquity UPLC BEH C18. The operation conditions are: injection volume is 3.5 µl; mobile phase is a gradient with Acetonitrile and ammonium bicarbonate 5 mM; pH is 8.5; the flow rate is 0.6 ml/min; wavelength is 280 nm; column temperature is 40° C. and sample temperature is 10° C.

An API useful in the dosage form of the invention can be one or more substances selected from the group consisting of gastrointestinal function conditioning agents, anti-inflammatory agents, analgesics, anti-migraines, antihistaminic agents, cardiovascular agents, diuretics, anti-hypertensive agents, anti-hypolipidemic agents, anti-ulcer agents, anti-emetics agents, anti-asthmatic agents, anti-depressants, vitamins, anti-thrombic agents, chemotherapeutic agents, hormones, anthelmintic agents, anti-diabetic agents, anti-viral agents and mixtures thereof.

In a particular embodiment, the physiologically active compound is a benzimidazole compound labile in an acid medium. In a further embodiment, the physiologically active compound is a benzimidazole derivative of formula (I), salts or stereoisomers thereof

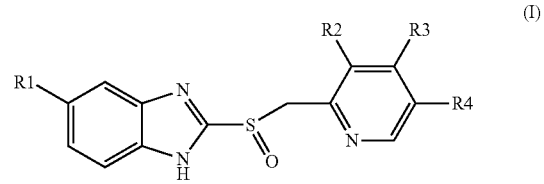

wherein
$R^1$ is hydrogen, methoxy or difluoromethoxy,
$R^2$ is methyl or methoxy,
$R^3$ is methoxy, 2,2,2-trifluoroethoxy or 3-methoxypropoxy, and
$R^4$ is hydrogen or methyl.

In a further embodiment, said benzimidazole derivative is lansoprazole, omeprazole, rabeprazole or pantoprazole, salts or stereosimers thereof. Preferably, the benzimidazole derivative is esomeprazole or its salts, in particular magnesium salt, sodium salt, calcium salt, lithium salt, potassium salt, or strontium salt. In yet a further embodiment, said physiologically active compound is esomeprazol sodium salt, i.e. the sodium salt of (−)-(S)-5-methoxy-2-[(4-methoxy-3,5-dimethylpyridin-2-yl)methylsulfinyl]-3H-benzoimidazole.

In a particular embodiment the physiologically active compound is present in an amount between 10% and 90%, more particularly between 30% and 85%, more particularly between 40% and 80%, more particularly between 50% and 75%, by weight with respect to the total weight of the core.

The core may additionally comprise further pharmaceutically acceptable excipients and/or inert beads (i.e. inert solid substance in the shape of a small ball) and/or an alkaline compound. The inert bead is a pharmaceutically inert substance in relation to the physiologically active compound. That is, it does not react with the physiologically active compound under the conditions used to cause its decomposition, and may consist of a sugar, such as saccharose, starch and the mixtures thereof. In a specific embodiment, said inert bead consists of cellulose, and has an average grain size of between 0.08 and 0.3 mm. In a particular embodiment the inert bead is present in an amount between 1% and 50%, more particularly between 10% and 40%, more particularly between 20% and 30%, by weight with respect to the total weight of the core.

In a specific embodiment, the core is present in the dosage form of the invention in an amount between 5% and 35%, more particularly between 10% and 20%, by weight with respect to the total weight of the unit.

In the particular case when a benzimidazole compound, stereoisomer or salt thereof such as esomeprazol is employed as an acid-labile API, the dosage form of the invention comprises enteric fine granules. This formulation is useful for the treatment and/or prevention of digestive ulcer (gastric ulcer, duodenal ulcer, anastomotic ulcer, etc. . . . ), gastritis, reflux esophagitis, eradication of *H. pylori*, suppression of gastrointestinal bleeding caused by digestive ulcer, acute stress ulcer and hemorrhagic gastritis, suppression of gastrointestinal bleeding caused by invasive stress, treatment and prevention of ulcer caused by non-steroidal anti-inflammatory agent, treatment and prevention of gastric hyperacidity and ulcer caused by postoperative stress. The dosage of the preparation per an adult is about 0.5 to 1.500 mg/day, preferably about 5 to 150 mg/day, as a benzimidazole compound, stereoisomer or salt thereof. Thus, dosage forms of the invention comprising said benzimidazole compounds are useful for the reduction of gastric acid secretions.

Separating Layer

An essential feature of the invention is the presence glyceryl monostearate in the separating layer.

In a preferred embodiment of the present invention, the glyceryl monostearate is present in the separating layer in an amount comprised between 2% and 60% in weight with respect to the total weight of water soluble polymer, and more preferably in an amount comprised between 8% and 18% in weight with respect to the total weight of water soluble polymer. In a further embodiment the glyceryl monostearate is present in the separating layer in an amount comprised between 2% and 10% in weight with respect to the total weight of water soluble polymer. In a further embodiment the glyceryl monostearate is present in the separating layer in an amount comprised between 2% and 8% in weight with respect to the total weight of water soluble polymer. In a further embodiment the glyceryl monostearate is present in the separating layer in an amount comprised between 2% and 5% in weight with respect to the total weight of water soluble polymer Also present in the separating layer, the water soluble polymer is any polymer which readily dissolves in water in neutral or almost neutral conditions, e.g. in the range of pH between 6 and 8.

The skilled person is aware of suitable water soluble polymers, and can easily find them in reference books and handbooks. For example, see pages 114-119 of "Encyclopedia of pharmaceutical technology, Volume I", Swarbrick, J.; Boylan, J.C.; Ed. Marcel Dekker, Inc., 2002, for a discussion on the general properties of water soluble polymers. Illustrative examples are Dextrans, pectin, carrageenan, guar gum, poly (beta-hydroxyethyl methacrylate), polyvinyl alcohol, polyacrylamide, hydroxyethyl cellulose, polyvinylpyrrolidone, polyethylene oxides (e.g. polyethylene glycol), soluble starchs (e.g. amylase), algynic acid and its alkaline salts (e.g. sodium or potassium salts), polylisine, hyaluronic acid, hydroxypropyl cellulose, hydroxypropyl methylcellulose, or carboxymethylcellulose and its alkaline salts (e.g. sodium carboxymethylcellulose). Also indication of the solubility of different polymers in water can be found in "Handbook of Pharmaceutical Excipients", Rowe, R.C.; Sheskey, P.J.; Quinn, M., Ed. Pharmaceutical Press and American Pharmacists Association, sixth edition, 2009.

According to a particular embodiment of the invention, said water soluble polymer is a cellulose, such as hydroxypropyl cellulose, hydroxypropyl methylcellulose, or carboxymethylcellulose and its alkaline salts (e.g. sodium carboxymethylcellulose). In a further embodiment, said water soluble polymer is hydroxypropyl methylcellulose.

In a particular embodiment, the separating layer is present in the dosage form of the invention in an amount between 5% and 45%, more particularly between 5% and 30%, more particularly between 7% and 20%, by weight with respect to the total weight of the dosage form.

Enteric Coating

Enteric coatings, their compositions and methods of preparation thereof are known in the art. The skilled person has many reference books and handbooks available on the subject, and can use any enteric coating available. See for example chapter 46 of "Remington, the science and practice of pharmacy", $21^{st}$ Edition, 2005, Ed. Lippincott Williams & Wilkins. According to an embodiment of the invention, said enteric coating is acidic. Enteric coatings comprise gastroresistant polymers, such as methacrylic copolymers, for example a copolymer formed by methacrylic acid and esters of methacrylic acid. Also, plasticisers such as triethyl acetate or the like, and one or more further pharmaceutically acceptable inert excipients, such as talc, may be included. In a specific embodiment, said enteric coating is present in the dosage form of the invention in an amount between 10% and 90%, more particularly between 20% and 85%, more particularly between 30% and 80%, more particularly between 50% and 75%, by weight with respect to the total weight of the dosage form.

Definitions and Additional Components

According to an embodiment of the invention, the dosage form of the invention may comprise at least one additional layer. In a further embodiment of the invention, the dosage form of the invention comprises a mechanical protective layer such as those described in WO2009/043926A2. In an embodiment of the invention, the dosage form of the invention comprises an additional layer which comprises a mixture of 2, 3 or 4 different polyethylenglycol polymers. According to an embodiment, said additional layer comprises a mixture of polyethylene glycol with an average molecular weight between 3,000 and 5,000, more preferably 4,000, polyethylene glycol with an average molecular weight between more than 5,000 and 7,000, more preferably 6,000 and polyethylene glycol with an average molecular weight between more than 7,000 and 9,000, more preferably 8,000.

According to a further embodiment, the dosage forms of the invention comprise an enteric coating which is a modified release composition.

The dosage forms and the tablets of the invention may comprise one or more excipients, including one or more plasticizers. The term "excipient" has the same meaning as that given in the *US Pharmacopoeia and National Formulary*, i.e. any component, other than the active substance(s) intentionally added to the formulation of a dosage form. Exemplary excipients are disintegrants, which act by swelling and/or wicking, lubricants, colorants, flavour masking agents, flavouring agents, stabilizers, binders, fillers, foaming agents, sweeteners, sweeteners, pore-forming agents, acids (e.g. citric or tartaric acid), sodium chloride, a bicarbonate (e.g. sodium or potassium), sugars and alcohols.

For the purposes of the invention, a "plasticizer" is a substance that is normally used to improve the mechanical properties of a film formed by a polymeric substance. It is a product which does not return to its original form after deformation. When added to a polymeric substance, plasticizers provide a material with improved resistance and flexibility. For the purposes of the present invention, plasticizers are preferably solid at room temperature and water soluble. Plasticizer agents can be selected from the group consisting of, a wax, linoline-type alcohols, a gelatine, a polyethylene glycol, a polypropylene glycol, triacetin, tributyl citrate, triethyl citrate, dibutyl sebacate, medium chain length triglyceride fatty acids, resin acid, long chain fatty acids (e.g. stearic acid, palmitic acid) or mixtures thereof. Other preferred plasticizer agents are those which also have lubricant characteristics such as glyceryl monostearate, stearic acid, glyceryl palmine stearate, glyceryl dibehenate and the like.

As examples of flavour masking agents, water insoluble polymers such as ethyl cellulose, polymers insoluble in saliva and soluble in gastric fluid such as a copolymer of methyl methacrylate, butyl methacrylate, and diethylaminoethyl methacrylate, and the like can be used.

By the term 'disintegrant' it is understood a substance which, upon addition to a solid preparation, facilitates its break-up or disintegration after administration and permits the release of an active ingredient as efficiently as possible to allow for its rapid dissolution. As examples of the disintegrating agent, starches such as corn starch and potato starch, partial alpha starch, sodium carboxymethyl starch, carmellose, carmellose calcium, crosscarmellose sodium, polyvinyl alcohol, crospovidone, low-substituted hydroxypropyl cellulose, crystalline cellulose, hydroxypropyl starch and the like can be given. Also, hydroxypropyl cellulose may be used as a disintegrant.

As examples of flavouring agents, perfume, lemon, lemon-lime, orange, menthol, peppermint oil, vanillin or powders of these absorbed with dextrin or cyclodextrin, and the like can be used.

As examples of the lubricant, magnesium stearate, magnesium stearate, fumarate stearyl, talc, stearic acid, colloidal silicon dioxide (Aerosil 200®), and the like can be given.

As examples of the colorant, food dyes such as food yellow No. 5, food red No. 3, food blue No. 2, food lake dye, red iron oxide, and the like can be given.

As examples of the stabilizer or solubilizer, antioxidants such as ascorbic acid and tocopherol, surfactants such as polysorbate 80 and the like can be given depending on the physiologically active component used.

As examples of the binder, hydroxypropyl methyl cellulose, carboxyvinyl polymer, carmellose sodium, alpha starch, polyvinylpyrrolidone, gum Arabic, gelatin, pullulan and the like can be given.

As examples of filler, sucrose, glucose, lactose, mannitol, xylitol, dextrose, microcrystalline cellulose, maltose, sorbitol, calcium phosphate, calcium sulphate and the like can be given.

As examples of the foaming agent, sodium bicarbonate can be used.

As examples of the sweetener, sodium saccharin, dipotassium glycyrrhizin, aspartame, stevia, thaumatin and the like can be given.

By the term 'solid dosage form', i.e. 'dosage form of the invention', it is understood a preparation in solid state such as a tablet, granule, capsule, minitablets, fine granules, coated layers, pellets, etc. . . .

By the term "pharmaceutically solid dosage form" it is understood a preparation in solid state such as a tablet, granule, capsule, minitablets, fine granules, coated layers, etc., which comprises a pharmaceutically active ingredient. According to a preferred embodiment, said dosage form is a pellet, a granule, a tablet or a mini-tablet. The dosage form of the invention may be produced following methods known in the art (see "Remington, the science and practice of pharmacy", 21$^{st}$ Edition, 2005, Ed. Lippincott Williams & Wilkins). According to a further aspect, the invention is directed to a process for the preparation of the dosage form of the invention, comprising an aqueous layering process, i.e. sequentially dispersing all the ingredients of a layer in water and then coating the dosage form with said dispersion.

For example, a review of the different methods for obtaining pellets for pharmaceutical purposes can be found in the book Pharmaceutical Pelletization Technology, edited by Isaac Ghebre-Sellassie, Marcel Dekker, Inc., 1989. In a particular embodiment, the dosage forms of the invention are obtained applying the different layers by means of conventional fluid bed coating techniques using aqueous solutions or suspensions of the components of such layers. Briefly, in a fluid bed apparatus inert nuclei are covered with a first layer that contains the physiologically active compound. Then, said layer is covered with the separating layer comprising a water soluble polymer and glyceryl monostearate, and then with the enteric coating. Any further coating is subsequently added in the same way.

EXAMPLES

Figure 1A:
FIG. 1a shows a picture of the solid dosage forms according to comparative example 3 of the present application after a storage of 6 days at 45° C. and 75% of relative humidity.
Figure 1A:
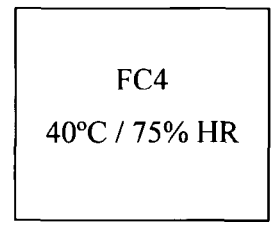

The following abbreviations have been used:
Hypromellose=hydroxypropyl methylcellulose (HPMC)
PEG nnnn=polyethylene glycol nnnn
Eudragit=methacrilic acid-ethyl acrylate copolymer (1:1)
Opadry II 85 F=commercial name of a partially hydrolyzed polyvinyl alcohol containing polymer Example 1

Separating Layer Comprising Hydroxypropyl Methylcellulose and Glyceryl Monostearate in Esomeprazole Sodium Pellets Comprising Three Layers Esomeprazole sodium pellets where prepared by spraying a suspension of each coat (FC) in the proportions shown in Table 1:

TABLE 1

|  |  | DESCRIPTION | 40 mg dose |
|---|---|---|---|
| CORE | Inert bead | Cellulose CP-102 | 23.1 |
|  | FC 1 | Esomeprazole sodium(*) | 42.6 |
|  | (API layer) | Hypromellose | 10.3 |
|  |  | Talc | 6.7 |
| FC 2 |  | Hypromellose | 24.4 |
| (separating layer |  | Titanium dioxide | 2.0 |
| according to |  | Glyceryl monostearate | 3.3 |
| invention) |  | Polysorbate 80 | 1.3 |
| FC 3 |  | Eudragit L30D-55 | 157.8 |
| (Enteric layer) |  | Triethyl citrate | 23.7 |
|  |  | Glyceryl monostearate | 7.9 |
|  |  | Polysorbate 80 | 3.2 |

(*)Equivalent to 40 mg esomeprazole base

Pellets were prepared by spraying a suspension of the components of Film Coating 1 (FC1) over the inert bead and drying in a fluid bed apparatus. That is, first the core was provided (inert bead+FC1). A dispersion with the components of the FC2 was prepared and sprayed over the core. Then, a dispersion of FC3 was sprayed over FC2. Each film coating (FC) was obtained by spraying the different aqueous suspension in a fluid bed apparatus at approximately 40° C. with further drying.

Example 2 (Comparative)

Separating Layer Comprising Hydroxypropyl Methylcellulose (No Glyceryl Monostearate) in Esomeprazole Sodium Pellets Comprising Three Layers Esomeprazole sodium pellets where prepared as in example 1 by spraying a suspension of each coat (FC) in the proportions shown in Table 2:

TABLE 2

|  |  | DESCRIPTION | 40 mg dose |
|---|---|---|---|
| CORE | Inert bead | Cellulose CP-102 | 25.4 |
|  | FC 1 | Esomeprazole sodium(*) | 42.5 |
|  | (API layer) | Hypromellose | 10.3 |
|  |  | Talc | 6.7 |
| FC 2 |  | Hypromellose | 4.1 |
| (separating layer) |  | Talc | 28.9 |
|  |  | Titanium dioxide | 2.0 |
| FC 3 |  | Eudragit L30D-55 | 122.7 |
| (Enteric layer) |  | Triethyl citrate | 12.3 |
|  |  | Glyceryl monostearate | 4.9 |
|  |  | Polysorbate 80 | 2.0 |

(*)Equivalent to 40 mg esomeprazole base

Example 3 (Comparative)

Separating Layer Comprising Partially Hydrolyzed Polyvinyl Alcohol in Esomeprazole Sodium Pellets Comprising Three Layers Esomeprazole sodium pellets where prepared as in example 1 by spraying a suspension of each coat (FC) in the proportions shown in Table 3:

TABLE 3

|  |  | DESPRIPTION | 40 mg dose |
|---|---|---|---|
| CORE | Inert bead | Cellulose CP-102 | 25.4 |
|  | FC 1 | Esomeprazole sodium(*) | 42.5 |
|  | (API layer) | Hypromellose | 10.3 |
|  |  | Talc | 6.7 |
| FC 2 |  | Opadry II 85 F | 32.7 |
| (separating layer) |  | Titanium dioxide | 2.0 |
| FC 3 |  | Eudragit L30D-55 | 122.7 |
| (Enteric layer) |  | Triethyl citrate | 18.4 |
|  |  | Glyceryl monostearate | 6.1 |
|  |  | Polysorbate 80 | 2.5 |

(*)Equivalent to 40 mg esomeprazole base

Example 4

Esomeprazole Sodium, FC4 Pellets

Esomeprazole sodium pellets of example 1-3 where further coated with a protection coat (FC4) as shown in table 4.

TABLE 4

| FC4 pellets | | |
|---|---|---|
|  | DESCRIPTION | 40 mg dose |
| FC3 pellets | Pellets of examples 1-3 | 306.7 |
| FC 4 | PEG 4000 | 46.9 |
| (over-coating | PEG 6000 | 33.4 |
| layer) | PEG 8000 | 86.1 |
|  | Glyceryl monostearate | 18.1 |

The resulting pellets were mixed with the compression base shown in Table 5 until a homogenous mixture was obtained. Then, the mixture was compressed to obtain a tablet which was coated with Opadry II. A hardness range between 5 and 8 kp was obtained and all tablets showed a friability less than 0.5% and having a disintegration time of about 10 minutes in water.

TABLE 5

| Components | 40 mg tablet(*) |
|---|---|
| FC4 Pellets of Esomeprazole Sodium | 491.9 |
| Microcrystalline cellulose | 245.9 |
| Crospovidone | 47.6 |
| Sodium stearyl fumarate | 7.9 |
| Total | 793.3 |

(*)Equivalent to esomeprazole base

Example 5

Stability Comparative Data of Examples 1-3

After 6 days in open dish at 40° C. and 75% RH, samples of the formulation of comparative example 3 where black while at the same conditions formulating of example 1 retained its original aspect, as stated in the following table 1.

TABLE 1

Stability study:

| FORMULATION | COMPOSITION | 40 mg dose | Coloration after 6 days 40° C./ 75% HR |
|---|---|---|---|
| Example 1 (Separating layer according to invention) | Hypromellose 2910 Titanium dioxide Glyceryl monostearate Potysorbate 80 | 24.4 2.0 3.3 1.3 | + |
| Example 3 (Separating layer according to prior art) | Opadry II 85 F Titanium dioxide | 32.7 2.0 | +++ |

− No colorations
+ Low coloration
++ Coloration
+++ High Coloration

Figure 1B:
FIG. 1b shows a picture of the solid dosage forms according to example 1 of the present application after storage of 6 days at 45° C. and 75% of relative humidity.

The results are also shown in FIGS. 1a and 1b, where it can be seen that after 6 days at 40° C. and 75% of relative humidity, solid dosage form according to the invention (example 1, FIG. 1b) still remain with the same colour, meaning no degradation of the active ingredient occurred, whereas solid dosage forms according to the prior art (example 3, FIG. 1a) turns black characterizing the degradation of the active ingredient due to acidic medium.

This clearly shows that the active ingredient, namely esomeprazole sodium salt, migrate from the internal FC1 layer to the enteric coating FC3. Said enteric layer being acidic, the active ingredient degrades and turn black.

The invention claimed is:

1. A pharmaceutical oral solid dosage form comprising (i) a core comprising esomeprazole sodium salt; (ii) a separating layer comprising a water soluble polymer and glyceryl monostearate in an amount between 2% and 60% by weight with respect to the total weight of water soluble polymer; and (iii) an enteric coating.

2. The dosage form according to claim 1, wherein said water soluble polymer is a cellulose.

3. The dosage form according to claim 1, comprising at least one additional layer.

4. The dosage form according to claim 3, wherein the additional layer comprises a mixture of 2, 3 or 4 different polyethyleneglycol polymers.

5. The dosage form according to claim 1, wherein said core comprises an inert bead and/or an alkaline compound.

6. The dosage form according to claim 1 which is a pellet, a granule, a tablet or mini-tablet.

7. A process for the preparation of a dosage form as defined in claim 1, comprising an aqueous layering process.

8. A method for treating and/or preventing digestive ulcer, gastritis, reflux esophagitis, eradication of *H. pylori*, suppression of gastrointestinal bleeding caused by digestive ulcer, acute stress ulcer and hemorrhagic gastritis, suppression of gastrointestinal bleeding caused by invasive stress, ulcer caused by non-steroidal anti-inflammatory agent, gastric hyperacidity or ulcer caused by postoperative stress, which method comprises administering to a patient in need of such treatment and/or prevention a dosage form as defined in claim 1.

9. A tablet comprising one or more pharmaceutically acceptable excipients and one or more dosage forms as defined in claim 1.

10. A capsule or sachet comprising one or more dosage forms as defined in claim 1.

11. The dosage form according to claim 2, wherein the water soluble polymer is hydroxypropyl methylcellulose.

12. A tablet comprising a pharmaceutically acceptable excipient and (i) a core comprising esomeprazole sodium salt; (ii) a separating layer comprising a water soluble polymer and glyceryl monostearate in an amount between 2% and 60% by weight with respect to the total weight of water soluble polymer; and (iii) an enteric coating.

* * * * *